(12) United States Patent
Jiang et al.

(10) Patent No.: US 7,183,309 B2
(45) Date of Patent: Feb. 27, 2007

(54) INDOLE DERIVATIVES USEFUL AS PROGESTERONE RECEPTOR MODULATORS

(75) Inventors: Weiqin Jiang, Raritan, NJ (US); James J. Fiordeliso, Raritan, NJ (US); Zhihua Sui, Raritan, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/255,444

(22) Filed: Oct. 21, 2005

(65) Prior Publication Data

US 2006/0111427 A1    May 25, 2006

Related U.S. Application Data

(60) Provisional application No. 60/622,582, filed on Oct. 27, 2004.

(51) Int. Cl.
  *A61K 31/404*   (2006.01)
  *C07D 209/04*   (2006.01)
(52) U.S. Cl. ...................................... 514/418; 548/452
(58) Field of Classification Search ................ 548/490, 548/491
  See application file for complete search history.

(56) References Cited

FOREIGN PATENT DOCUMENTS

| EP | 1051179 B1 | 9/2005 |
|----|------------|--------|
| WO | WO 99/43672 A1 | 9/1999 |
| WO | WO 00/66555 A1 | 11/2000 |
| WO | WO 02/083126 A1 | 10/2002 |

OTHER PUBLICATIONS

STN search report of WO 2001032621 (Nishimura et al.).*
International Search Report for International Appln. No. PCT/US2005/037817.
Fensome, A. et al.: "New Progesterone Receptor Antagonists: 3,3-Disubstituted-5-aryloxindoles", Bioorganic & Medicinal Chem. Letters 12 (2002), pp. 3487-3490.

* cited by examiner

*Primary Examiner*—Joseph K. McKane
*Assistant Examiner*—Yong Chu

(57) ABSTRACT

The present invention is directed to novel indole derivatives, pharmaceutical compositions containing them and their use in the treatment or prevention of disorders and diseases mediated by agonists and antagonists of the progesterone receptor. The clinical uses of these compounds are related to contraception, the treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate, or minication of side effects of cyclid menstrual bleeding. Additional uses of the invention include stimulation of food intake.

4 Claims, No Drawings

INDOLE DERIVATIVES USEFUL AS PROGESTERONE RECEPTOR MODULATORS

RELATED APPLICATION

This application claims the benefit of U.S. Provisional Application No. 60/622,582, filed Oct. 27, 2004, which is incorporated herein by reference in its entirety.

FIELD OF THE INVENTION

The present invention is directed to novel indole derivatives, the pharmaceutical compositions containing them and their use in the treatment or prevention of disorders and diseases mediated by agonists and antagonists of the progesterone receptor. The clinical usage of these compounds are related to contraception, the treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

BACKGROUND OF THE INVENTION

Intracellular receptors are a class of structurally related proteins involved in the regulation of gene proteins. Steroid receptors are a subset of these receptors, including the progesterone receptors (PR), androgen receptors (AR), estrogen receptors (ER), glucocorticoid receptors (GR) and mineralocorticoid receptors (MR). Regulation of a gene by such factors requires the intracellular receptor and a corresponding ligand which has the ability to selectively bind to the receptor in a way that affects gene transcription.

Progesterone receptor modulators (progestagens) are known to play an important role in mammalian development and homeostasis. Progesterone is known to be required for mammary gland development, ovulation and the maintenance of pregnancy. Currently, steroidal progestin agonists and antagonists are clinically approved for contraception, hormone replacement therapy (HRT) and therapeutic abortion. Moreover, there is good preclinical and clinical evidence for the value of progestin antagonists in treating endometriosis, uterine leiomyomata (fibroids), dysfunctional uterine bleeding and breast cancer.

The current steroidal progestagens have been proven to be quite safe and are well tolerated. Sometimes, however, side effects (e.g. breast tenderness, headaches, depression and weight gain) have been reported that are attributed to these steroidal progestagens, either alone or in combination with estrogenic compounds.

Steroidal ligands for one receptor often show cross-reactivity with other steroidal receptors. As an example, many progestagens also bind to glucocorticoid receptor. Non-steroidal progestagens have no molecular similarity with steroids and therefore one might also expect differences in physicochemical properities, pharmacokinetic (PK) parameters, tissue distribution (e.g. CNS versus peripheral) and, more importantly, non-steroidal progestagens may show no/less cross-reactivity to other steroid receptors. Therefore, non-steroidal progestagens will likely emerge as major players in reproductive pharmacology in the foreseeable future.

It was known that progesterone receptor existed as two isoforms, full-length progesterone receptor isoform (PR-B) and its shorter counterpart (PR-A). Recently, extensive studies have been implemented on the progesterone receptor knockout mouse (PRKO, lacking both the A- and B-forms of the receptors), the mouse knockoutting specifically for the PR-A isoform (PRAKO) and the PR-B isoform (PRBKO). Different phenotypes were discovered for PRKO, PRAKO and PRBKO in physiology studies in terms of fertility, ovulation uterine receptivity, uterine proliferation, proliferation of mammary gland, sexual receptivity in female mice, sexual activity in male mice and infanticide tendencies in male mice. These findings provided great challenge for synthetic chemists to construct not only selective progesterone receptor modulator (SPRM), but also PR-A or PR-B selective progesterone receptor modulator.

SUMMARY OF THE INVENTION

The present invention provides novel trisubstituted thiophenes of the formula (I):

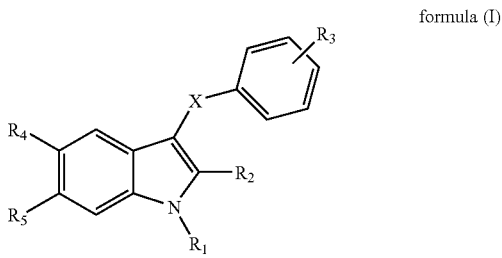

formula (I)

wherein:

X=S, S(O) or $SO_2$;

$R_1$ is selected from the group consisting of hydrogen, $C_{1-8}$ alkyl, cycloalkyl, aralkyl and heteroaryl-alkyl, wherein the cycloalkyl, aralkyl or heteroaryl-alkyl group is optionally substituted with one or more substituents independently selected from the group consisting of halogen, hydroxy, alkyl, alkoxy, $NO_2$, $CF_3$, CN and $CO_2H$;

$R_2$ is $C_{1-8}$ alkyl or $C_{2-8}$ alkenyl optionally substituted by one or more of methyl, hydroxy or $CH_2OH$, or $R_2$ is aryl optionally substituted with $CF_3$, CN, $NO_2$, $C_{1-8}$ alkyl or $OC_{1-8}$ alkyl, provided that when $R_2$ is optionally substituted $C_{1-8}$ alkyl, or $C_{2-8}$ alkenyl then $R_4$ and $R_5$ cannot be halogen;

$R_3$ is hydrogen, $NO_2$, halogen, $C_{1-8}$ alkyl, CN or $CF_3$;

$R_4$ is halogen, $NO_2$ or CN;

$R_5$ is halogen or $CF_3$;

provided that $R_4$ is $NO_2$ or CN when $R_5$ is $CF_3$, and $R_4$ is halogen when $R_5$ is halogen; and a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by one or more progesterone receptors in a subject in need thereof comprising administering to the subject a therapeutically effective amount of any of the compounds or pharmaceutical compositions described above.

Illustrating the invention is a method of contraception comprising administering to a subject in need thereof co-therapy with a therapeutically effective amount of a compound of formula (I) with an estrogen or estrogen antagonist.

Another example of the invention is the use of any of the compounds described herein in the preparation of a medicament for treating: (a) dysfunctional bleeding, (b) endometriosis, (c) uterine leiomyomata, (d) secondary amenorrhea, (e) polycystic ovary syndrome, (f) carcinomas and adenocarcinomas of the endometrium, ovary, breast, colon, prostate (g) minication of side effects of cyclid menstrual bleeding and for (h) contraception and (i) stimulation of food intake in a subject in need thereof.

DETAILED DESCRIPTION OF THE INVENTION

The present invention is directed to a compound of formula (I):

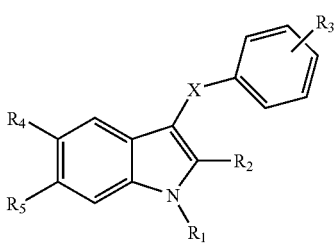

wherein X, $R_1$, $R_2$, $R_3$, $R_4$ and $R_5$ are as herein defined, useful for the treatment of disorders mediated by an progesterone receptor. More particularly, the compounds of the present invention are useful for the treatment and prevention of disorders mediated by the progesterone-A and progesterone-B receptors. More preferably, the compounds of the present invention are tissue selective progesterone receptor modulators.

The compounds of the present invention are useful in the treatment of disorders associated with the depletion of progesterone, hormone sensitive cancers and hyperplasia, endometriosis, uterine fibroids, osteoarthritis and as contraceptive agents, alone or in combination with an estrogen or estrogen agonist.

The compounds of the present invention are useful in the treatment of disorders associated with the depletion of progesterone, secondary amenorrhea, dysfunctional bleeding, uterine leiomyomata, endometriosis; polycystic ovary syndrome, carcinomas and adenocarcinomas of the endometrium, ovary, breast, colon, prostate and as contraceptive agents, alone or in combination with a estrogen or estrogen antagonist.

In one embodiment of the present invention are compounds of formula (I) wherein X is S. In another embodiment of the present invention are compounds of formula (I) wherein X is $SO_2$.

In a preferred embodiment of the present invention $R_1$ is selected from the group consisting of hydrogen, lower alkyl and aralkyl. More preferably, R1 is selected from hydrogen and lower alkyl. In another preferred embodiment of the present invention, $R_1$ is hydrogen.

In an embodiment of the present invention, $R_3$ is selected from hydrogen and $NO_2$.

In an embodiment of the present invention, $R_4$ is selected from halogen, CN or nitro group.

In an embodiment of the present invention, $R_5$ is selected from $CF_3$ or halogen.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

As used herein, the term "progestogen antagonist" shall include mifepristone, J-867 (Jenapharm/TAP Pharmaceuticals), J-956 (Jenapharm/TAP Pharmaceuticals), ORG-31710 (Organon), ORG-33628 (Organon), ORG-31806 (Organon), onapristone and PRA248 (Wyeth).

As used herein, unless otherwise noted, "halogen" shall mean chlorine, bromine, fluorine and iodine.

As used herein, unless otherwise noted, the term "alkyl" whether used alone or as part of a substituent group, should include straight and branched chain compositions of one to eight carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1–4 carbon atoms. Similarly, the group "-(alkyl)$_{0-4}$-", whether alone or as part of a large substituent group, shall mean the absence of an alkyl group or the presence of an alkyl group comprising one to four carbon atoms. Suitable examples include, but are not limited to —$CH_2$—, —$CH_2CH_2$—, $CH_2$—$CH(CH_3)$—, $CH_2CH_2CH_2$—, —$CH_2CH(CH_3)CH_2$—, $CH_2CH_2CH_2CH_2$—, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocyclic aromatic groups such as phenyl, naphthyl, and the like.

As used herein, unless otherwise noted, "aralkyl" shall mean any lower alkyl group substituted with an aryl group such as phenyl, naphthyl and the like. Suitable examples include benzyl, phenylethyl, phenylpropyl, naphthylmethyl, and the like.

As used herein, unless otherwise noted, the term "cycloalkyl" shall mean any stable 3–8 membered monocyclic, saturated ring system, for example cyclopropyl, cyclobutyl, cyclopentyl, cyclohexyl, cycloheptyl and cyclooctyl.

As used herein, unless otherwise noted, the term "cycloalkyl-alkyl" shall mean any lower alkyl group substituted with a cycloalkyl group. Suitable examples include, but are not limited to cyclohexyl-methyl, cyclopentyl-methyl, cyclohexyl-ethyl, and the like.

As used herein, unless otherwise noted, the terms "acyloxy" shall mean a radical group of the formula —O—C(O)—R where R is alkyl, aryl or aralkyl, wherein the alkyl, aryl or aralkyl is optionally substituted. As used herein, the term "carboxylate" shall mean a radical group of the formula —C(O)O—R where R is alkyl, aryl or aralkyl, wherein the alkyl, aryl or aralkyl is optionally substituted.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, unless otherwise noted, the term "heterocycloalkyl-alkyl" shall mean any lower alkyl group substituted with a heterocycloalkyl group. Suitable examples include, but are not limited to piperidinyl-methyl, piperazinyl-methyl, piperazinyl-ethyl, morpholinyl-methyl, and the like.

When a particular group is "substituted" (e.g., cycloalkyl, aryl, heteroaryl, heterocycloalkyl), that group may have one or more substituents, preferably from one to five substituents, more preferably from one to three substituents, most preferably from one to two substituents, independently selected from the list of substituents. Additionally when aralkyl, heteroaryl-alkyl, heterocycloalkyl-alkyl or cycloalkyl-alkyl group is substituted, the substituent(s) may be on any portion of the group (i.e. the substituent(s) may be on the aryl, heteroaryl, heterocycloalkyl, cycloalkyl or the alkyl portion of the group.)

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylC$_1$–C$_6$alkylaminocarbonylC$_1$–C$_6$alkyl" substituent refers to a group of the formula

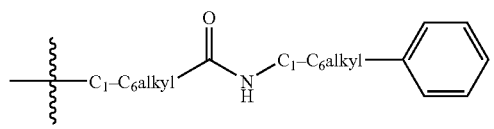

Abbreviations used in the specification, particularly the Schemes and Examples, are as follows

| | |
|---|---|
| Ac = | Acetyl group (—C(O)—CH$_3$) |
| DMF = | Dimethyl formamide |
| Et = | ethyl (i.e. —CH$_2$CH$_3$) |
| EtOAc = | Ethyl acetate |
| FBS = | Fetal bovine serum |
| HPLC = | High pressure liquid chromatography |
| HRT = | Hormone replacement therapy |
| iPr$_2$NH = | Diisopropylamine |
| MeOH = | Methanol |
| Ph = | Phenyl |
| TEA or Et$_3$N = | Triethylamine |
| TBSOTf = | Tert-Butyldimethylsilyl triflate |
| DCM = | Dichloromethane |
| THF = | Tetrahydrofuran |
| Ts = | Toluene sulfonyl |
| Ms = | Methyl sulfonyl |
| DABCO = | 1,4-Diazabicyclo[2,2,2]octane |
| TEA = | Triethyl amine |

The synthesis of typical structures is shown in the following Scheme.

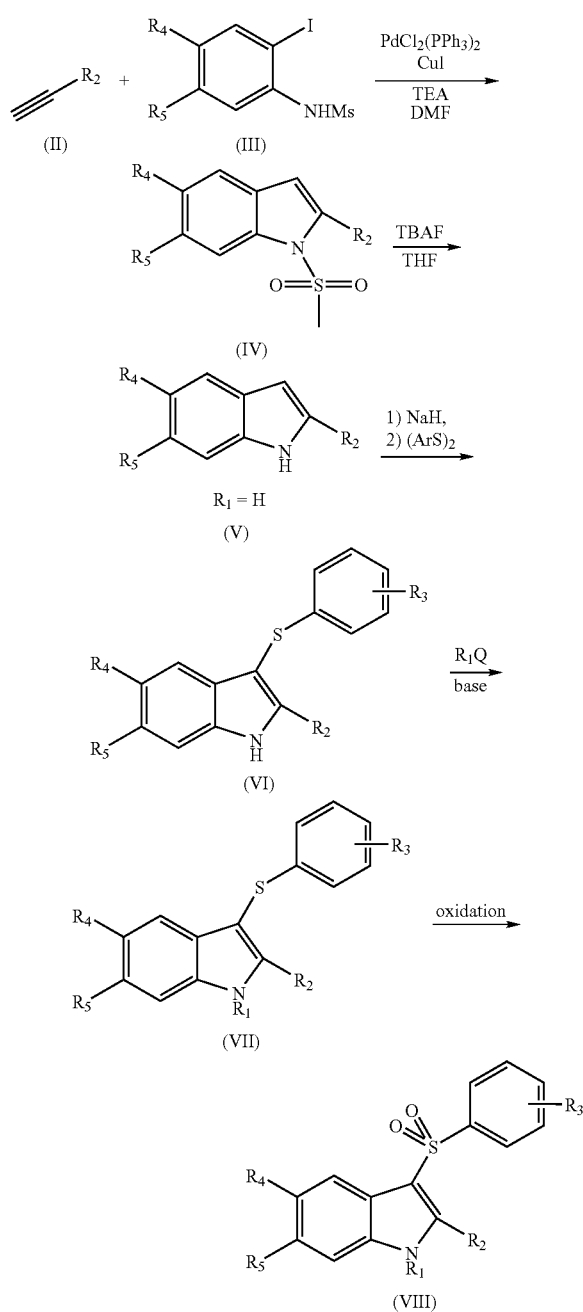

More particularly, a suitably substituted compound of formula (III), where $R_4$ and $R_5$ are $NO_2$, $CF_3$, CN or halogen, a known compound or compound prepared by known methods, is reacted with a compound of formula (II), a known compound, in the presence of palladium (+2) catalyst, such as $Pd(OAc)_2$ plus $PPh_3$, $PdCl_2(PPh_3)_2$, $PdCl_2(dppf)_2$ and the like, in the presence of an organic base such as DIPEA, TEA, DEBCO and the like, in an organic solvent such as 1,4-dioxalane, THF, DME, DMSO and the like, at a temperature in the range of about 0 to 45° C., to yield the corresponding compound of formula (IV). The reaction of compound II and III can be effected by various coupling reactions including Sonogashira reaction. The deprotection of compound IV with a cleaving reagent, such as TBAF or NaOMe in MeOH yielded compound V.

The compound of formula (V) is reacted with a suitably substituted compound of formula $(ArS)_2$, a known compound, in the presence of base, such as NaH, KOtBu, KH and the like, at a temperature in the range of 0 to 50° C., to yield the corresponding compound of formula (VI).

The compound of formula (VI) is reacted with $R_1Q$ in the presence of base, such as $Et_3N$, pyridine, DABCO or $Na_2CO_3$, $K_2CO_3$ and the like, to generate compound of formula (VII); where Q is a leaving group such as Cl, Br, I, Ts or Ms group.

The compound of formula (VII) is oxidized with peroxide such as $H_2O_2$, m-CPBA, tBuOOH and the like to generate compound of formula (VIII).

One skilled in the art will recognize that it may be necessary and/or desirable to protect $R^1$, $R^2$, $R^3$, $R^4$ or $R^5$ group at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Wherein the present invention directed to co-therapy comprising administration of one or more compound(s) of formula I and a progestogen or progestogen antagonist, "therapeutically effective amount" shall mean that amount of the combination of agents taken together so that the combined effect elicits the desired biological or medicinal response. For example, the therapeutically effective amount of co-therapy comprising administration of a compound of formula I and progestogen would be the amount of the compound of formula I and the amount of the progestogen that when taken together or sequentially have a combined effect that is therapeutically effective. Further, it will be recognized by one skilled in the art that in the case of co-therapy with a therapeutically effective amount, as in the example above, the amount of the compound of formula I and/or the amount of the progestogen or progestogen antagonist individually may or may not be therapeutically effective.

As used herein, the term "co-therapy" shall mean treatment of a subject in need thereof by administering one or more compounds of formula I with a progestogen or progestogen antagonist, wherein the compound(s) of formula I and progestogen or progestogen antagonist are administered by any suitable means, simultaneously, sequentially, separately or in a single pharmaceutical formulation. Where the compound(s) of formula I and the progestogen or progestogen antagonist are administered in separate dosage forms, the number of dosages administered per day for each compound may be the same or different. The compound(s) of formula I and the progestogen or progestogen antagonist may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or perispinal routes of administration by delivery via intracranial or intravertebral needles and/or catheters with or without pump devices. The compound(s) of formula I and the progestogen or progestogen antagonist may be administered according to simultaneous or alternating regimens, at the same or different times during the course of the therapy, concurrently in divided or single forms.

As used herein, the term "composition" is intended to encompass a product comprising the specified ingredients in the specified amounts, as well as any product which results, directly or indirectly, from combinations of the specified ingredients in the specified amounts.

TABLE 1

[Structure: indole with $R_4$, $R_5$ on benzene ring; $R_2$ at 2-position; X-phenyl-$R_3$ at 3-position; NH]

| | X | $R_2$ | $R_3$ | $R_4$ | $R_5$ | MF |
|---|---|---|---|---|---|---|
| 1 | S | –C(CH₃)(OH)–CH=CH₂ | H | $NO_2$ | $CF_3$ | $C_{23}H_{21}FN_2O_3S$ |
| 2 | S | –C(CH₃)=CH₂ | H | $NO_2$ | $CF_3$ | $C_{23}H_{21}ClN_2O_3S$ |
| 3 | S | Ph | 4-$NO_2$ | F | Cl | $C_{23}H_{21}N_3O_5S$ |
| 4 | S | –C(CH₃)(OH)–CH=CH₂ | 3-$NO_2$ | CN | $CF_3$ | $C_{19}H_{22}N_2O_3S$ |
| 5 | S | Ph | H | F | Cl | $C_{23}H_{22}N_2O_3S$ |
| 6 | S | Ph | 3-$NO_2$ | F | Cl | $C_{24}H_{24}N_2O_4S$ |
| 7 | $SO_2$ | Ph | 3-$NO_2$ | F | Cl | $C_{25}H_{20}F_6N_2O_3S$ |
| 8 | $SO_2$ | Ph | H | F | Cl | $C_{24}H_{24}N_2O_4S$ |

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. It is further intended that when m is >1, the corresponding $R^4$ substituents may be the same or different.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "prodrug" forms, which, when administered in such form, convert to the active moiety in vivo.

This invention includes pharmaceutical compositions comprising one or more compounds of this invention, preferably in combination with one or more pharmaceutically acceptable carriers and/or excipients. The invention also includes methods of contraception and methods of treating or preventing maladies associated with the progesterone receptor, the methods comprising administering to a mammal in need thereof a pharmaceutically effective amount of one or more compounds as described above wherein R is alkyl, aryl, heteroary or alkylaryl group.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, genign prostatic hypertrophy; carcinomas and adenocarcinomas of the endometrium, ovary, breast, colon, prostate, pituitary, meningioma and other hormone-depent tumors. Additional uses of the present progesterone receptor antagonists include the synchronization of the estrus in livestock.

When used in contraception the progesterone receptor antagonists of the current invention may be used either alone in a continuous administration of between 0.1 and 500 mg per day, or alternatively used in a different regimen which would entail 2–4 days of treatment with the progesterone receptor antagonist after 21 days of a progestin. In this regimen between 0.1 and 500 mg daily doses of the progestin (e.g. levonorgestrel, trimegestone, gestodene, norethistrone acetate, norgestimate or cyproterone acetate) would be followed by between 0.1 and 500 mg daily doses of the progesterone receptor antagonists of the current invention.

The progesterone receptor agonists of this invention, used alone or in combination, can also be utilized in methods of contraception and the treatment and/or prevention of dysfunctional bleeding, uterine leiomyomata, endometriosis; polycystic ovary syncrome, carcinomas and adenocarcimomas of the endometrium, ovary, breast, colon, prostate. Additional uses of the invention include stimulation of food intake.

When used in contraception the progesterone receptor agonists of the current invention are preferably used in combination or sequentially with an estrogen agonist (e.g. ethinyl estradiol). The preferred dose of the progesterone receptor agonist is 0.01 mg and 500 mg per day.

This invention also includes pharmaceutical compositions comprising one or more compounds described herein, preferably in combination with one or more pharmaceutically acceptable carriers or excipients. When the compounds are employed for the above utilities, they may be combined with one or more pharmaceutically acceptable carriers, or excipients, for example, solvents, diluents and the like and may be administered orally in such forms as tablets, caplules, dispersible powders, granules, or suspensions containing, for example, from about 0.05 to 5% of suspending agent, syrups containing, for example, from about 10 to 50% of sugan, and elixirs containing, for example, from 20 to 50% ethanol, and the like, or parenterally in the form of sterile injectale solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in dibided doses two to four times a day, or in a sustained release from. For most large mammals, the total daily dosage is from about 1 to 100 mg, preferably from about 2 to 80 mg Dosage froms suitable for internal use comprise from about 0.5 to 500 mg of the active compound in intimate admixture with a solid or liquid pharmaceutically acceptable carrier. This dosage regimen may be adjusted to provide the optimal therapeutic respose. For example, several divided doses may be administered daily or the dose may be proportionally reduced as indicated by the exigencies of the therapeutic situation.

These active compounds may be administered orally as well as by intervenous, imtramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oil, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hardfilled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxylpropoycellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions of dispersions. In all cases, the form must be sterile and must be fluid to the extent that easy syring ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The following non-limiting examples illustrate preparation and use of the compounds of the invention.

EXAMPLE 1

2-(5-Nitro-3-phenylsulfanyl-6-trifluoromethyl-1H-indol-2-yl)-propan-2-ol

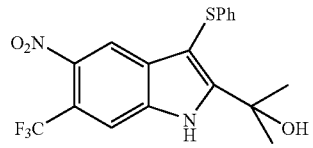

2-(5-Nitro-6-trifluoromethyl-1H-indol-2-yl)-propan-2-ol (192 mg, 0.667 mmol) was stirred with $(PhS)_2$ (320 mg, 1.467 mmol) in DMF (4 mL). After 64 hours, the reaction was worked up by taking up in EtOAc/water. Organic layer was washed with brine several times. The organic layer was dried, concentrated and purified by silica gel column (55% EtOAc/hexane) to give the title compound (19 mg, 10%) with recovered starting material (50 mg).

$^1$H NMR (CDCl$_3$) δ 9.71 (s, 1H), 8.17 (s, 1H), 7.85 (s, 1H), 7.16 (m, 2H), 7.10 (m, 1H), 6.95 (d, 2H, J=8.8 Hz), 1.81 (s, 6H); MS (m/z): 395 (MH$^-$). HRMS: calcd. M$^+$ for $C_{18}H_{15}F_3N_2O_3S$ 396.0755. found 396.0760.

EXAMPLE 2

2-Isopropenyl-5-nitro-3-phenylsulfanyl-6-trifluoromethyl-1H-indole

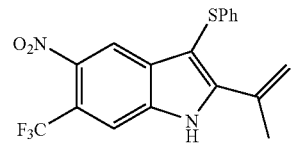

2-(3-Iodo-5-nitro-6-trifluoromethyl-1H-indol-2-yl)-propan-2-ol (263 mg, 0.635 mmol) and CuSPh (330 mg, 1.9 mmol) was stirred in DMF (2 mL) for 16 hours at 100° C. After normal aqueous work-up (EtOAc/water), purification on silica gel (5%–20% EtOAc/Hexane) provided title compound as white solid (18 mg, 8%), together with another product, 2-(5-nitro-3-phenylsulfanyl-6-trifluoromethyl-1H-indol-2-yl)-propan-2-ol (35 mg, 14%). $^1$H NMR (CDCl$_3$) δ 8.20 (s, 1H), 7.91 (s, 1H), 7.01–7.25 (m, 5H), 5.81 (s, 1H), 5.42 (s, 1H), 2.32 (s, 3H); MS (m/z): 377 (MH$^-$); HRMS: calc'd MH$^+$ for $C_{23}H_{21}ClN_2O_3S$ 378.0650. found 378.0649.

EXAMPLE 3

6-Chloro-5-fluoro-3-(4-nitro-phenylsulfanyl)-2-phenyl-1H-indole

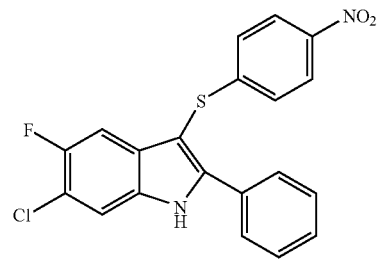

To a solution of 6-chloro-5-fluoro-2-phenyl-1H-indole (24 mg, 0.10 mmol) in DMF (1.0 mL) was added NaH (60% dispersion in mineral oil, 6.0 mg, 0.15 mmol). After 30 min at room temperature, a solution of 4-nitrophenyl disulfide (34 mg, 0.11 mmol) in THF (0.8 mL) was added. After 1 hour, the reaction mixture was quenched with water (5 mL). After extracted with EtOAc (2×30 mL), the organic layers were dried over MgSO₄ and concentrated. The crude product was purified on silica gel column (5% EtOAc/hexane) to provide title compound as a white solid (36 mg, 90%). $^1$H NMR (CDCl$_3$) δ 9.12 (s, 1H), 8.02 (d, 2H, J=10.0 Hz), 7.68–7.40 (m, 5H), 7.74 (m, 2H), 7.12 (d, 2H, J=10.0 Hz). MS (m/z): 397 (MH⁻).

EXAMPLE 4

1A. tert-Butyl-(1,1-dimethyl-prop-2-ynyloxy)-dimethyl-silane

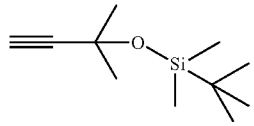

2-Methyl-but-3-yn-2-ol (2.20 g, 26.2 mmol) in DCM (50 mL) was mixed with 2,6-lutadine (9.1 mL, 78.6 mmol). TBSOTf (6.6 mL, 28.8 mmol) was added to the reaction mixture slowly. After 2 hours at room temperature, an extra amount of TBSOTf (1.5 mL) was added. After 16 hours at room temperature, the reaction was quenched with 10% HOAc aqueous solution (400 mL). The product was extracted with DCM (2×200 mL). The combined organic layers were washed with brine, dried and concentrated. Purification of the crude on silica gel column (Foxy, 3:7 EtOAc/Hexane) provided desired product as colorless liquid (4.12 g, 80%). $^1$H NMR (CDCl$_3$) δ 2.58 (s, 1H), 0.82 (s, 6H).

1B. 2-[1-(tert-Butyl-dimethyl-silanyloxy)-1-methyl-ethyl]-6-trifluoromethyl-1H-indole-5-carbonitrile

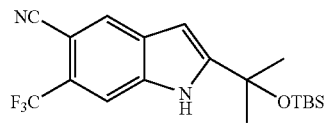

N-(4-Cyano-2-iodo-5-trifluoromethyl-phenyl)-methanesulfonamide (1.95 g, 5.0 mmol), tert-Butyl-(1,1-dimethyl-prop-2-ynyloxy)-dimethyl-silane (992 mg, 5.0 mmol), PdCl$_2$(PPh$_3$)$_2$, (175 mg, 0.25 mmol), CuI (95 mg, 0.5 mmol), NEt$_3$ (1.4 mL, 10.0 mmol), was mixed in DMF (15 mL) and stirred at room temperature for 16 hours. Water was added and the mixture was extracted twice with ethyl acetate. The organic layers were washed with 10% LiCl solution, dried over magnesium sulfate, filtered, evaporated to a brown oil. The brown oil was purified by column chromatography eluting with 1, 3, and 10% ethyl acetate/hexanes. The product was obtained as a white solid (306 mg, 16%). $^1$H NMR (CDCl$_3$) δ 8.75 (s, 1H), 7.92 S, 1H), 7.67 (s, 1H), 6.27 (d, J=1.2 Hz, 1H), 1.58 (s, 6H), 0.85 (s, 9H), 0.3 (s, 6H). MS (m/z): 405 (MNa⁺), 381 (MH⁻).

C. 2-[1-(tert-Butyl-dimethyl-silanyloxy)-1-methyl-ethyl]-3-(3-nitro-phenylsulfanyl)-6-trifluoromethyl-1H-indole-5-carbonitrile

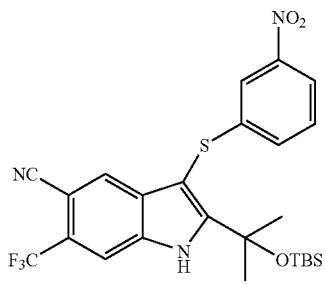

The title compound was prepared in 63% yield according to the procedure described in Example 3 starting from 3-nitrophenyl disulfide and 2-[1-(tert-butyl-dimethyl-silanyloxy)-1-methyl-ethyl]-6-trifluoromethyl-1H-indole-5-carbonitrile. MS (m/z): 534 (MH⁻).

D. 2-(1-Hydroxy-1-methyl-ethyl)-3-(3-nitro-phenylsulfanyl)-6-trifluoromethyl-1H-indole-5-carbonitrile

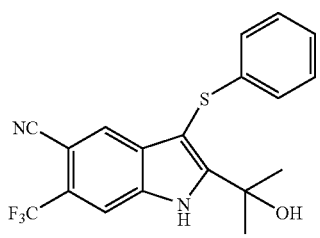

2-[1-(tert-Butyl-dimethyl-silanyloxy)-1-methyl-ethyl]-3-(3-nitro-phenylsulfanyl)-6-trifluoromethyl-1H-indole-5-carbonitrile (33 mg, 0.060 mmole) was stirred in THF (1 mL) with TBAF (1M in THF) (0.1 mL, 0.1 mmol). The reaction was allowed to proceed overnight and purified by column chromatography eluting with 0 and 1% methanol/dichloromethane. Obtained 17 mg (71%) of desired product. $^1$H NMR (acetone-d$_6$) δ 11.75 (s, 1H), 8.19 (s, 1H), 8.08 (s, 1H), 7.98–7.96 (m, 1H), 7.81 (t, J=2.0 Hz, 1H), 7.54 (t. J=8.0 Hz, 1H), 7.48–7.45 (m, 1H), 2.83 (s, 1H), 1.75 (s, 6H). MS (m/z): 444 (MNa⁺), 420 (MH⁻).

EXAMPLE 5

6-Chloro-5-fluoro-2-phenyl-3-phenylsulfanyl-1H-indole

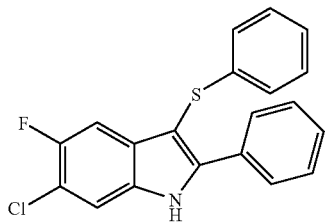

The title compound was prepared in 64% yield according to the procedure described in Example 3 starting from phenyl disulfide. $^1$H NMR (CDCl$_3$) δ 8.50 (s, 1H), 7.75–7.73 (m, 2H), 7.48–7.39 (m, 4H), 7.34 (d, J=9.2, 1H), 7.20–7.16 (m, 2H), 7.10–7.05 (m, 3H). MS (m/z): 352 (MH⁻).

EXAMPLE 6

6-Chloro-5-fluoro-3-(3-nitro-phenylsulfanyl)-2-phenyl-1H-indole

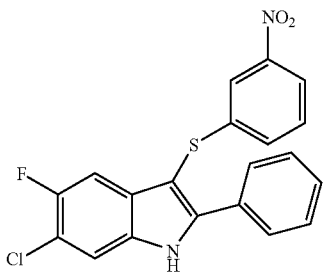

The title compound was prepared in 54% yield according to the procedure described in Example 4 starting from 3-nitrophenyl disulfide. $^1$H NMR (CDCl$_3$) δ 8.70 (s, 1H), 7.90 (m, 1H), 7.84 (t, J=1.2 Hz, 1H), 7.72–7.70 (m, 2H), 7.52 (d, J=5.9, 1H), 7.47–7.45 (m, 3H), 7.34–7.29 (m, 3H). MS (m/z): 421 (MNa$^+$), 397 (MH$^-$).

EXAMPLE 7

6-Chloro-5-fluoro-3-(3-nitro-benzenesulfonyl)-2-phenyl-1H-indole

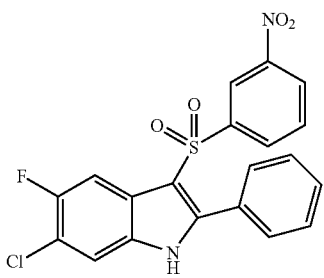

A solution of 6-chloro-5-fluoro-3-(3-nitro-phenylsulfanyl)-2-phenyl-1H-indole (45 mg, 0.11 mmol) in dichloromethane (10 mL) was prepared with most of the material soluble. To this solution was added m-chloroperoxybenzoic acid (60 mg, 0.242 mmol, estimate at 70% pure). The solution was not homogeneous, a white solid had precipitated out. The mixture was stirred overnight at room temperature. The solution became clear and brown in color. To the solution was added 1M sodium carbonate aqueous solution and dichloromethane. The layers were separated and the aqueous layer was extracted with dichloromethane. The organic layers were dried over magnesium sulfate, filtered, evaporated, and the residue purified by column chromatography eluting with 20% ethyl acetate/hexane. The product was obtained as a white solid (34 mg, 72%). $^1$H NMR (acetone-d$_6$) δ 12.60 (s, 1H), 8.06 (d, J=10.2 Hz, 1H), 7.71–7.64 (m, 5H), 7.59–7.42 (m, 6H). MS (m/z): 384 (MH$^-$).

Anal. calc'd for C$_{20}$H$_{13}$ClFNO$_2$S, C, 62.26; H, 3.40; N, 3.63. found, C, 61.12; H, 3.25; N, 3.52.

EXAMPLE 8

6-Chloro-5-fluoro-3-(3-nitro-benzenesulfonyl)-2-phenyl-1H-indole

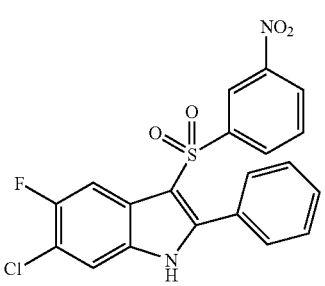

The title compound was prepared according to the procedure described in Example 7 starting from 6-chloro-5-fluoro-3-(3-nitro-phenylsulfanyl)-2-phenyl-1H-indole. $^1$H NMR (acetone-d$_6$) δ 11.75 (s, 1H), 8.39–8.36 (m, 1H), 8.27 (t, J=1.9 Hz, 1H), 8.11–8.07 (m, 2H), 7.76 (t, J=8.0 Hz, 1H), 7.70 (d, J=6.3 Hz, 1H), 7.63–7.50 (m, 5H). MS (m/z): 431 (MH$^+$), 429 (MH$^-$).

TABLE 1

| Ex | X | R$_2$ | R$_3$ | R$_4$ | R$_5$ | MF | inh. @ 3 uM | IC50 (nM) |
|---|---|---|---|---|---|---|---|---|
| 1 | S | —C(CH$_3$)$_2$OH | H | NO$_2$ | CF$_3$ | C$_{23}$H$_{21}$FN$_2$O$_3$S | 99% | 62 nM |

TABLE 1-continued

[Structure: indole with R4, R5 on benzene ring, R3-phenyl connected via X at 3-position, R2 at 2-position, NH]

| Ex | X | R₂ | R₃ | R₄ | R₅ | MF | inh. @ 3 uM | IC50 (nM) |
|---|---|---|---|---|---|---|---|---|
| 2 | S | isopropenyl | H | NO₂ | CF₃ | $C_{23}H_{21}ClN_2O_3S$ | | >10,000 |
|  | S | isopropenyl | H | F | Cl | | 86% | 306 |
| 3 | S | Ph | 4-NO₂ | F | Cl | $C_{23}H_{21}N_3O_5S$ | 88% | 1395 |
| 4 | S | C(CH₃)₂OH | 3-NO₂ | CN | CF₃ | $C_{19}H_{22}N_2O_3S$ | 69% | 2190 |
| 5 | S | Ph | H | F | Cl | $C_{23}H_{22}N_2O_3S$ | 103% | 1761 |
| 6 | S | Ph | 3-NO₂ | F | Cl | $C_{24}H_{24}N_2O_4S$ | 99% | 1900 |
| 7 | SO₂ | Ph | 3-NO₂ | F | Cl | $C_{25}H_{20}F_6N_2O_3S$ | 55% | 3622 |
| 8 | SO₂ | Ph | H | F | Cl | $C_{24}H_{24}N_2O_4S$ | 82% | 3181 |

EXAMPLE 9

In Vitro Testing-T47 D Assay

T47D human breast cancer cells are grown in RPMI medium without phenol red (Invitrogen) containing 10% (v/v) heat-inactivated fetal bovine serum (FBS; Hyclone), 1% (v/v) penicillin-streptomycin (Invitrogen), 1% (w/v) glutamine (Invitrogen), and 10 mg/mL insulin (Sigma). Incubation conditions are 37° C. in a humidified 5% (v/v) carbon dioxide environment. For assay, the cells are plated in 96-well tissue culture plates at 10,000 cells per well in assay medium [RPMI medium without phenol red (Invitrogen) containing 5% (v/v) charcoal-treated FBS (Hyclone) and 1% (v/v) penicillin-streptomycin (Invitrogen)]. Two days later, the medium is decanted and the compounds are added in a final concentration of 0.1% (v/v) dimethyl sulfoxide in fresh assay medium. Twenty-four hours later, an alkaline phosphatase assay is performed using a SEAP kit (BD Biosciences Clontech, Palo Alto, Calif.). Briefly, the medium is decanted and the cells are fixed for 30 minutes at room temperature with 5% (v/v) formalin (Sigma). The cells are washed once with room temperature Hank's buffered saline solution (Invitrogen). Equal volumes (0.05 mL) of 1× Dilution Buffer, Assay Buffer and 1:20 substrate/enhancer mixture are added. After 1-hour incubation at room temperature in the dark, the lysate is transferred to a white 96-well plate (Dynex) and luminescence is read using a LuminoSkan Ascent (Thermo Electron, Woburn, Mass.).

EXAMPLE 10

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of formula (I):

formula (I)

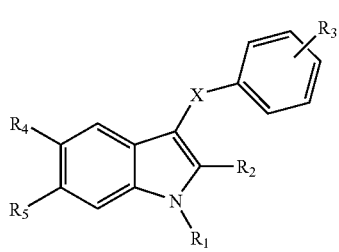

wherein:
X=SO₂;
R₁ is hydrogen;
R₂ is $C_{1-8}$ alkyl or $C_{2-8}$ alkenyl optionally substituted by CH₂OH;
R₃ is hydrogen or CF₃;
R₄ is halogen, NO₂ or CN;
R₅ is halogen or CF₃;

provided that $R_4$ is $NO_2$ or CN when $R_5$ is $CF_3$, and $R_4$ is halogen when $R_5$ is halogen; and
a pharmaceutically acceptable salt thereof.

2. A compound as in claim 1 wherein
X is $SO_2$, $R_1$ is hydrogen, $R_2$ is 2-propan-2-ol group or 2-Isopropenyl group, $R_3$ is hydrogen, $R_4$ is $NO_2$ or CN, $R_5$ is $CF_3$.

3. The compound of claim 1 is 2-(5-Nitro-3-phenylsulfanyl-6-trifluoromethyl-1H-indol-2-yl)-propan-2-ol.

4. A pharmaceutical composition comprising a pharmaceutically acceptable carrier and a compound of claim 1.

* * * * *